United States Patent [19]

Mallett

[11] Patent Number: 5,993,802
[45] Date of Patent: Nov. 30, 1999

[54] **PROCESS FOR BIOLOGICAL CONTROL OF *CALAMAGROSTIS CANADENSIS* USING A LOW TEMPERATURE BASIDIOMYCETE**

[75] Inventor: Kenneth I. Mallett, Alberta, Canada

[73] Assignee: Minister of Natural Resources as represented by the Canadian Forest Service, Ottawa, Canada

[21] Appl. No.: 08/889,157

[22] Filed: Jul. 7, 1997

[51] Int. Cl.$^6$ .................................................. A12N 63/00
[52] U.S. Cl. ...................... 424/93.5; 435/254.1; 435/911; 504/117
[58] Field of Search ........................ 424/93.5; 435/254.1, 435/911; 504/117

[56] References Cited

FOREIGN PATENT DOCUMENTS 4442255  5/1996  Germany .

OTHER PUBLICATIONS

Gaudet, D.A., Can J. Plant Pathol., 8:394–399, 1986.
Au Sholberg et al., Can J Plant Pathol 14 (3). 1992. 221–226.
Gaudet et al., Can J Plant Pathol 12 (1). 1990. 31–37.
Schreiner et al., Canadian Journal of Plant Pathology 17 (4). 1995. 362.

*Primary Examiner*—Irene Marx
*Attorney, Agent, or Firm*—J. Wayne Anderson

[57] ABSTRACT

The invention disclosed relates to a substantially biologically pure isolate of a low temperature basidiomycelte (LTB) fungus, (≡*Coprinus psychromorbidus*), to a delivery composition comprising the fungus and an agriculturally acceptable carrier capable of supporting growth of the fungus, and to a method for suppressing the growth of *Calmagrostis canadensis* and other related weed grasses which are hosts to LTB snow mould.

9 Claims, 4 Drawing Sheets

_5,993,802_

PROCESS FOR BIOLOGICAL CONTROL OF *CALAMAGROSTIS CANADENSIS* USING A LOW TEMPERATURE BASIDIOMYCETE

FIELD OF THE INVENTION

This invention relates to the use of a selected strain of a low temperature basidiomycete LTB snow mould (≡*Coprinus psychromorbidus*) as a bio-control agent of *Calamagrostis canadensis* and other related weed grasses which are hosts to LTB snow mould, and to a composition and method of delivery therefor.

BACKGROUND OF THE INVENTION

*Calmagrostis canadensis* (Michx.) Beauv. also known as bluejoint, is a grass plant that poses a serious threat to white spruce regeneration in reforestation areas. In cut-over. *C. canadensis* quickly spreads by means of rhizomes and seed to cover much of the site. The grass grows thick and tall thus out-competing white spruce for resources such as light, water and nutrients.

To date site preparation techniques and grazing have failed to control *C. canadensis*. Herbicides may be effective but their use has been extremely limited due to environmental concerns. Other weed species have been successfully controlled with plant pathogens., for example northern jointvetch by *Colletotrichum gloeosporiodes* f.sp. *aeschynomene*.

A variety of mycoherbicides have been proposed to control specific weeds. for example, Canadian Patent Number 1,224,055 (Watson et al, Jul. 14, 1987) describes the use of *Colletotrichum coccodes* for controlling velvetleaf and U.S. Pat. No. 4,643,756 (Cardina et al, Feb. 17, 1987) describes the use of *C. truncatum* for controlling Florida beggarweed. U.S. Pat. No. 4,776,873 (Caulder et al, Oct. 11, 1988) teaches a synergistic herbicidal composition comprising *Altemaria cassiae* and chemical herbicides for controlling sicklepod.

*C. canadensis* has been shown to be controlled by the microbes *C. calamagrostidis, F. nivalis* and mutants thereof. See commonly assigned U.S. Pat. No. 5,472,690. A drawback of this technology is that it is somewhat reliant on environmental factors such as free moisture on the leaf surface, for infection to occur.

The low temperature basidiomycete (LTB) fungus, was first described as a pathogen of C. by Lebeau and Logsdon (1958) Snow Mould of forage crops in Alaska and Yukon. Phytopathology, 48: 148–15. This fungus is psychrophilic and will only grow and parasitize plants under a snow cover. It is native to the boreal forest and so is not considered an introduced species. The fungus is not known to produce spores but spreads by vegetative growth.

Bio-control of *C. canadensis* and other related monocot species which are known to be hosts of LTB through use of the LTB fungus presents a good opportunity for controlling these grasses. The fungus does not necessarily have to kill the grass for it to be effective as reduced growth of grass plants would allow white spruce seedlings time to grow above the grass canopy.

Some preliminary work by our group with low temperature basidiomycete (LTB) fungii was described in Biocontrol of bluejoint grass (*Calamagrostis canadensis*) using low-temperature basidiomycete (LTB) K. A. Schreiner et al, Canadian Journal of Plant Pathology, volume 17, 1995. There is no description in this abstract of the selected LTB strain, the delivery composition, or the delivery method according to the invention.

SUMMARY OF THE INVENTION

It is an object of the invention to provide a selected LTB snow mould strain effective against *C. canadensis,* and other related monocot species which are hosts to snow mould.

It is another object of the present invention to provide a novel delivery composition and method for the delivery of LTB snow mould to a target plant.

According to one aspect of the invention, a substantially biologically pure isolate of a low temperature basidiomycete fungus (≡*Coprinus psychromorbidus*) having the identifying characteristics of *Coprinus psychromorbidus* (58719) ATCC Deposit accession no. 74407, is provided.

The deposit was made with the American Type Culture Collection (ATCC), 10801 University Blvd., Manassas, Va. 20110-2209 on Apr. 9, 1997 under the provisions of the Budapest Treaty.

According to another aspect of the invention, a composition for suppressing *C. canadensis* and other related monocot species which are hosts to LTB snow mould, comprising an effective amount of a substantially biologically pure isolate of a low temperature basidiomycete fungus having the identifying characteristics of ATCC Deposit Accession no. 74407, and an agriculturally acceptable carrier capable of supporting growth of the fungus, is provided.

According to yet another aspect of the invention, a method is provided for suppressing the growth of *C. canadensis* and other related monocot species which are hosts to LTB snow mould, comprising applying thereto or to the locus thereof in the autumn, an effective amount of a substantially biologically pure isolate of a low temperature basidiomycete fungus having the identifying characteristics of ATCC Deposit Accession no. 74407, and an agriculturally acceptable carrier capable of supporting growth of the fungus, wherein prior to application, the fungus is grown in the dark on the carrier at about 15° C. until the carrier is substantially thoroughly colonized by the fungus.

DETAILED DESCRIPTION OF THE PREFERRED EMBODIMENTS

It has been found that in order for the LTB snow mould to be effective, an agriculturally acceptable carrier capable of supplementing the growth of the fungus is required. The preferred carrier comprises sterilized cereal grains. A useful carrier composition comprises rye . . . 50–100%/w and oats . . . 0–50%/w. A 1:1 ratio of rye:oats is preferred.

The LTB snow mould infested grain is distributed over the locus of *C. canadensis* in the autumn. After snowfall when the grass plants are dormant, the LTB snow mould grows onto the target plants and causes disease. Affected grass plants are either killed or show reduced vigor the following growing season. This process provides a rapid and dramatic increase in the amount of LTB snow mould fungus present at the site through the addition of the LTB snow mould infested grain and the distribution process, and is a major advantage over other known biological herbicides.

More specifically, the LTB snow mould fungus previously isolated from nature in the boreal or subalpine forest is taken from pure culture and inoculated into a 1:1 mixture of sterilized rye and oat grains. The dimensions of the grain are in the range of 0.5–1.5×0.3–5 cm. The grain is sterilized in autoclavable plastic bags using an autoclave set at 121° C. and 1.4 kg $cm^{-2}$ for 2 hours. After the oat/rye grain mixture is cooled to ambient the fungus is introduced to the sterile grain using aseptic technique and is grown in the dark at 12–18° C., preferably about 15° C., for about one month ie. until the grain is substantially thoroughly colonized by the fungus. The LTB snow mould infested oat/rye grain mixture is taken to the site of Calamagrostis infestation and is distributed over the locus in the autumn of the year. Distribution can be done either by hand or mechanically. Optionally, the grain may be ground into a flour (preferably to a size that will pass a 25 mm sieve) after colonization, and the flour may be suspended in water and applied as a foliar spray. A rate of 6–50 g. preferably about 30 g., of infested oat/rye grain or flour mixture per L of water per $m^2$ Is used. The LTB snow mould grows from the infested grain onto the *Calamagrostis canadensis* and causes disease, after snow fall.

Experimental Data

An isolate of the low temperature basidiomycete (≡*Coprinus psychromorbidus*) (LTB-013) deposited with ATCC under accession no.-74407, was used for inoculations. *Calamagrostis canadensis* plants grown in the lab in 12.7 cm pots that had been "hardened off" were inoculated with 50 mL of LTB snow mould infested rye/oat grain distributed over the soil surface and covered with moistened cotton batten to simulate snow cover. Check ("uninoculated") plants had 50 mL of sterilized oat/rye mixture distributed over the soil surface before being covered with moistened cotton batten. The pots were placed individually in plastic bags and then incubated in a low temperature growth chamber at −5° C. for 12 weeks in the dark. The plants were then removed from the growth chamber and warmed to ambient in the dark for 48 hours. They were then placed on a bench in a glasshouse with 18 hours of light at 23° C. for 4 weeks. The plants were then evaluated for mortality and dry weight measurements were made for root and foliar biomass.

There was 12% mortality in the LTB snow mould inoculated grass plants. Foliar biomass dry weight of the snow mould inoculated plants was 67% of the check grass plants. Root biomass dry weight was 64% of the check grass plants. The differences between the biomass dry weight of the inoculated versus the check plants were statistically significant (P=0.05). These results show that the LTB fungus is pathogenic to *C. canadensis* causing both mortality and growth loss.

In further experiments, the LTB isolate LRS-013 (ATCC no. 74407) used throughout the field trial portion of the study, and a different (≡*C. psychromorbidus*) isolate LRS-064, used in the growth chamber study, was obtained from Dr. D. Gaudet of the Lethbridge Research Station, Agriculture and Agri-food Canada. Inoculum was prepared by homogenizing a 2 week-old LTB culture grown on potato dextrose agar in 250 mL of sterile distilled water. Fifty mL of the homogenate was added to a 1.7 L jar containing equal parts of rye and oat grains that had previously been sterilized. The inoculated grain was incubated for at least a month at 15° C. and then stored at −10° C. until used.

Field Plot Inoculations

Field Trial 1

The trial was conducted on three sites in Alberta and two sites in Saskatchewan. The three sites in Alberta were located near Whitecourt and the two sites in Saskatchewan were located near Candle lake. *Calamagrostis canadensis* was the dominant plant species at all five sites. At each site, five replications consisting of 5 inoculum level treatments including a check (no LTB) were established. Replications were kept at least 50 m apart. Plant identification and density data were collected prior to inoculation in the summer of 1993 and post inoculation in the summer of 1994 and 1995. Stems and leaves of *C. canadensis* were collected in the fall of 1994, 1995, and 1996 to determine dry weight.

Field Trial 2

A second field trial was established in the fall of 1994 at two sites near Whitecourt, Alberta to compare two different types of inoculum. One site had recently been harvested (in 1993) and the other was one of the same sites used in field trial 1 (Whitecourt 63). Two treatments were applied. The first consisted of the inoculum being applied as a flour (50 $g/m^2$), the check was sterile flour (50 $g/m^2$). The second treatment's inoculum consisted of aspen wood chips coated with fungus infested flour (50 $g/m^2$), the check was sterile flour coated wood chips (50 $g/m^2$). Five replicates of each treatment were established at each site. Plant identification and density data were collected prior to inoculation in the summer of 1994. Grass foliage was collected in the fall of 1995 and air dried before weighing.

Growth Chamber Experiments

Experiment 1

Plants from three clones of blue joint were dug from cutblocks located near Whitecourt, Alberta and brought back to the laboratory. Pieces of rhizomes with buds were placed in 12.7 cm flower pots, containing limed peat moss. The plants were grown under 18 hours of day length at day- and night-time temperatures of 25° C. and 20° C. respectively. The plants were watered twice weekly and fertilized with 20—20—20 fertilizer once a week. The grass plants were grown for ten weeks before being moved to outside the greenhouse to "harden-off" for three weeks.

The LTB fungus was grown on rye/oat grains for two months and then ground into a flour using a Wiley mill. The flour (10 ml/pot) was applied directly on the grass plants. Infested flour was also used to coat pieces of sterile aspen wood chips. The flour-coated wood chips (10 ml/pot) were applied to the grass. The check treatments were sterile four and sterile flour-coated wood chips. The pots were then covered with moistened absorbent cotton to simulate snow cover and placed in 10 L polyethylene bags before being moved to a darkened low temperature growth chamber kept at −6° C. Grass plants were incubated for 14 weeks in the low temperature growth chamber before being removed and placed in the greenhouse. The grass plants were then grown for two weeks under the greenhouse conditions outlined above. After four weeks the plants were unpotted and foliage was separated from roots before drying in an oven at 60° C. for one week and then weighing. The experiment was designed as a randomized complete block with four replications.

Experiment 2

Two clones of *C. canadensis* from the Whitecourt area were grown in pots in the greenhouse and hardened off as described above. The plants were inoculated with either LRS-013, LRS-064, NOF 001 and NOF-006 or a check treatment of sterilized oat/rye grains. Isolates. NOF-001 and NOF-006 were isolates of an unidentified snow mould fungus collected from *C. canadensis* near Whitecourt. Sixteen plants were inoculated with one of the five treatments, covered with moistened cotton batten, and placed in a low temperature growth chamber for 14 weeks. The plants were then placed in the greenhouse and grown for two weeks under the greenhouse conditions described above. After four weeks the plants were unpotted and foliage was separated from roots before drying in an oven at 60° C. for one week and then weighing. The experiment was designed as a randomized complete block with four replications.

RESULTS

Field Plot Studies

Analysis of the data showed that there was no effect of the fungus on four of the five cutblocks. Poor inoculum or rodent feeding were the causes attributed for the failure of LTB to control grass on these sites. These sites were not examined in 1995 nor 1996.

Figure 1:
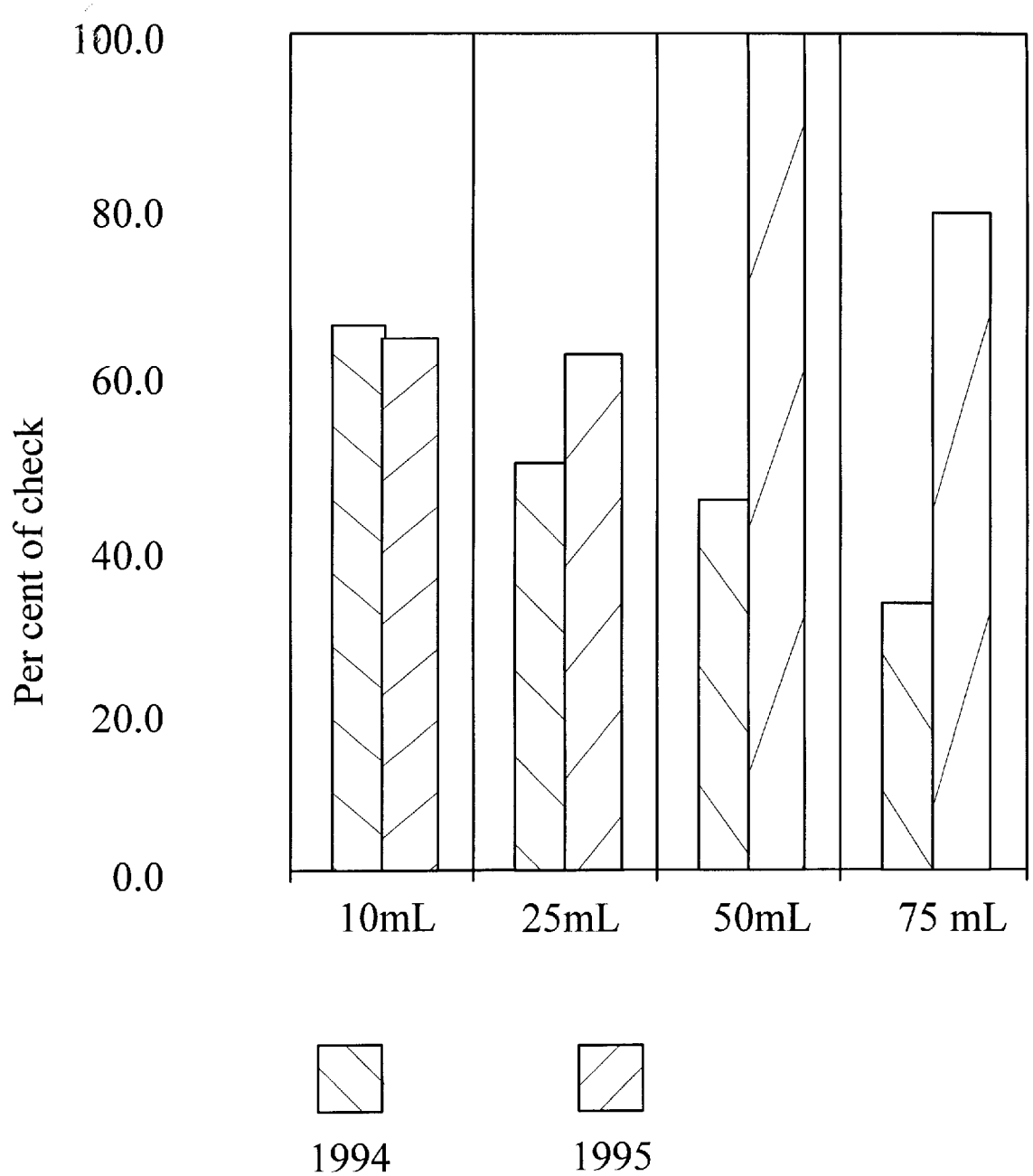
FIG. 1 is a graph which illustrates the effect of different volumes of LTB fungus on field grown *C. canadensis,* as a percentage of cover for 1994 and 1995.

Whitecourt cutblock 63 had significant differences in the percent cover of *C. canadensis* in the first year after application but not in the second year, FIG. 1. The dry weight of the grass in all treatments except the 50 mL treatment was less than the check, FIG. 2. This trend has occurred for three years after application. The 50 mL treatment on this cutblock did not reduce dry weight as much as expected. This may have been caused by poor inoculum and/or rodent feeding on the inoculum.

The forb/shrub biomass increased with LTB treatment in two of the five cutblocks, in the others there was no significant difference. Species diversity was variable; however, on the cutblock that LTB successfully reduced grass growth, species richness increased slightly as did forb dry weight as a percentage of the check.

Figure 3:
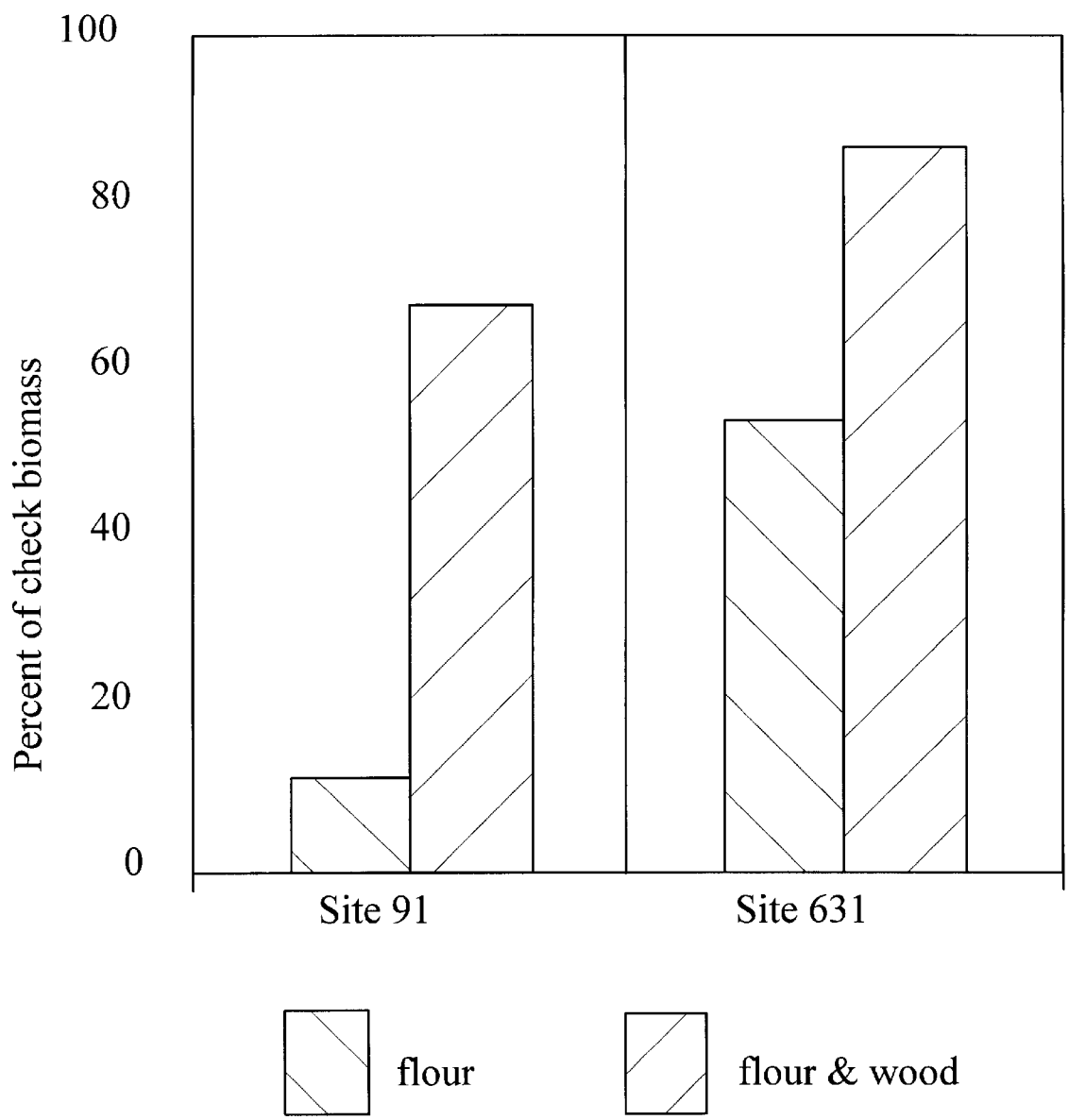
FIG. 3 is a graph which illustrates the effect of different LTB fungus inoculum on the foliar biomass of *C. canadensis* at two sites, 91 and 631.

The second field trial indicted that the flour inoculum controlled the grass at least as well as the oat/rye grains, FIG. 3. The flour coated wood did not control the grass as well as the flour or the oat/rye grains. The flour inoculum reduced the grass biomass significantly on a site that had recently been harvested and the grass was just becoming established.

Growth Chamber Studies

Figure 4:
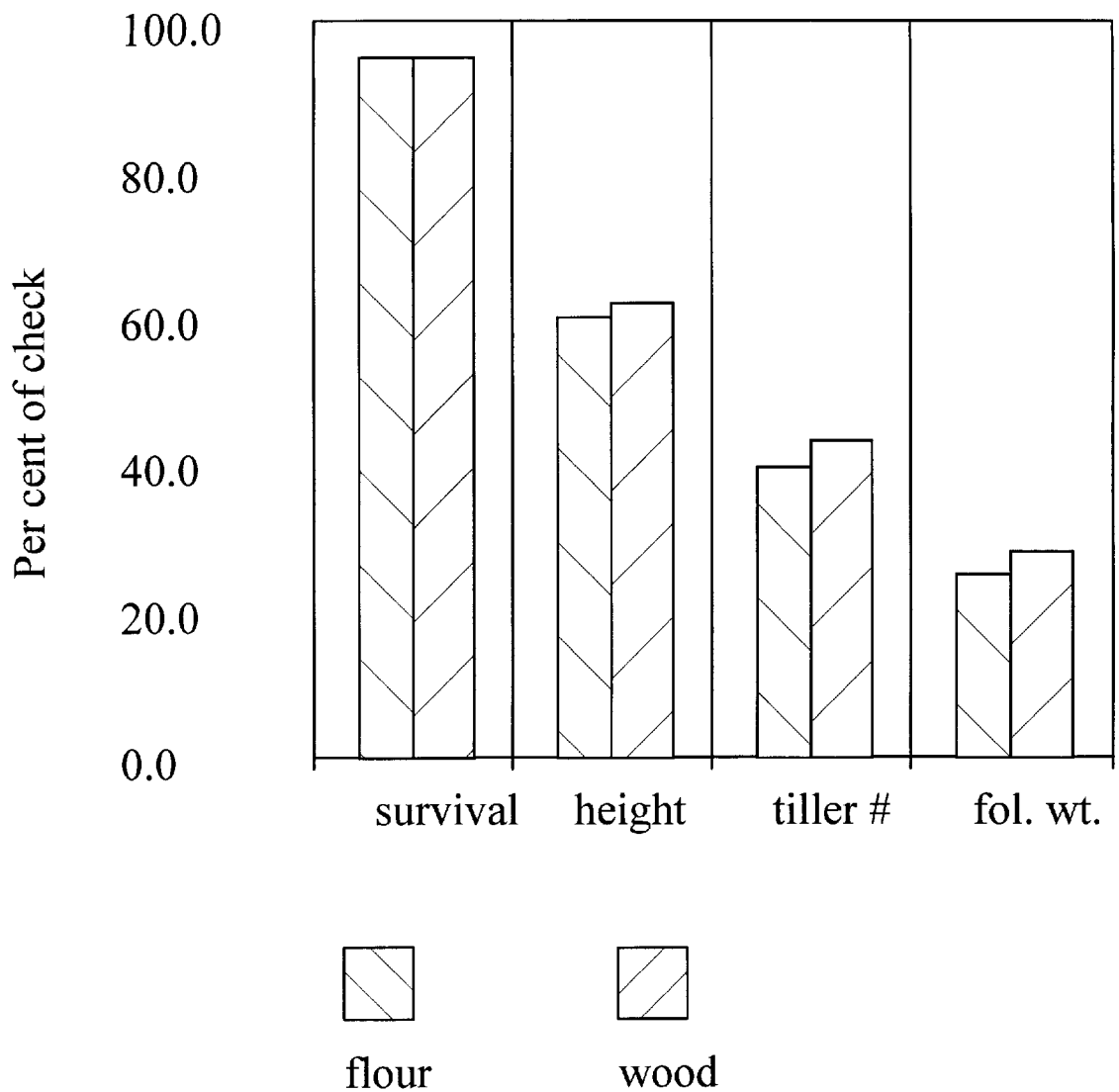
FIG. 4 is a graph which illustrates the effect of different LTB fungus inoculum on *C. canadensis* survival, height, tiller number and shoot dry weight, as a percentage of the check after 14 weeks incubation.

The results of growth chamber experiment 1 are shown in FIG. 4. Both inoculum types reduced inoculated *C. canadensis* plants survival, height, tiller number and foliar dry weight significantly from that of the check plants. There was no difference in the incidence of mortality, height, tiller number, or foliar dry weight between plants treated with the LTB infested flour and the LTB infested flour-coated wood.

The second growth chamber experiment showed that both LTB isolates were equally pathogenic to *C. canadensis* (Table 1). There was no significant difference between the two LTB isolates and their effect on *C. canadensis* foliar dry weight. The two unidentified snow mould isolates from Whitecourt were pathogenic to one clone of *C. canadensis* but not to the other. This is likely due to the fact that the clones of *C. Canadensis* may vary in their resistance to these isolates. Fruiting bodies of the unidentified snow mould have not been found. It is suspected, based on colony morphology, the fungus is a basidiomycete.

TABLE 1

Dry weights of two greenhouse-grown *Calamagrostis canadensis* clones treated with sterile grain (check), two LTB isolates (LRS-013 and LRS-064), and two isolates of an unidentified snow mould (NOF-001 and NOF-006)

| Treatment | Foliar dry weight (in grams) | Root dry weight (in grams) | Rhizome dry weight (in grams) |
| --- | --- | --- | --- |
| Clone 1 (Check) | 0.87(±0.07)* | 1.4(±0.3) | 0.64(±0.08) |
| Clone 2 (Check) | 0.87(±0.09) | 1.3(±0.3) | 0.40(±0.08) |
| Clone 1 (LRS-013) | 0.18(±0.07) | 1.4(±0.3) | 0.47(±0.08) |
| Clone 2 (LRS-013) | 0.15(±0.07) | 1.0(±0.3) | 0.27(±0.08) |
| Clone 1 (LRS-064) | 0.23(±0.07) | 1.9(±0.3) | 0.35(±0.08) |
| Clone 2 (LRS-064) | 0.09(±0.08) | 0.92(±0.3) | 0.36(±0.08) |
| Clone 1 (NOF-001) | 1.07(±.07) | 2.1(±0.3) | 0.61(±0.08) |
| Clone 2 (NOF-001) | 0.46(±.07) | 0.67(±0.3) | 0.32(±0.08) |
| Clone 1 (NOF-006) | 0.80(±.07) | 1.7(±0.3) | 0.60(±0.08) |
| Clone 2 (NOF-006) | 0.55(±.07) | 1.3(±0.3) | 0.42(±0.08) |

*Standard error of the mean

Discussion

Figure 2:
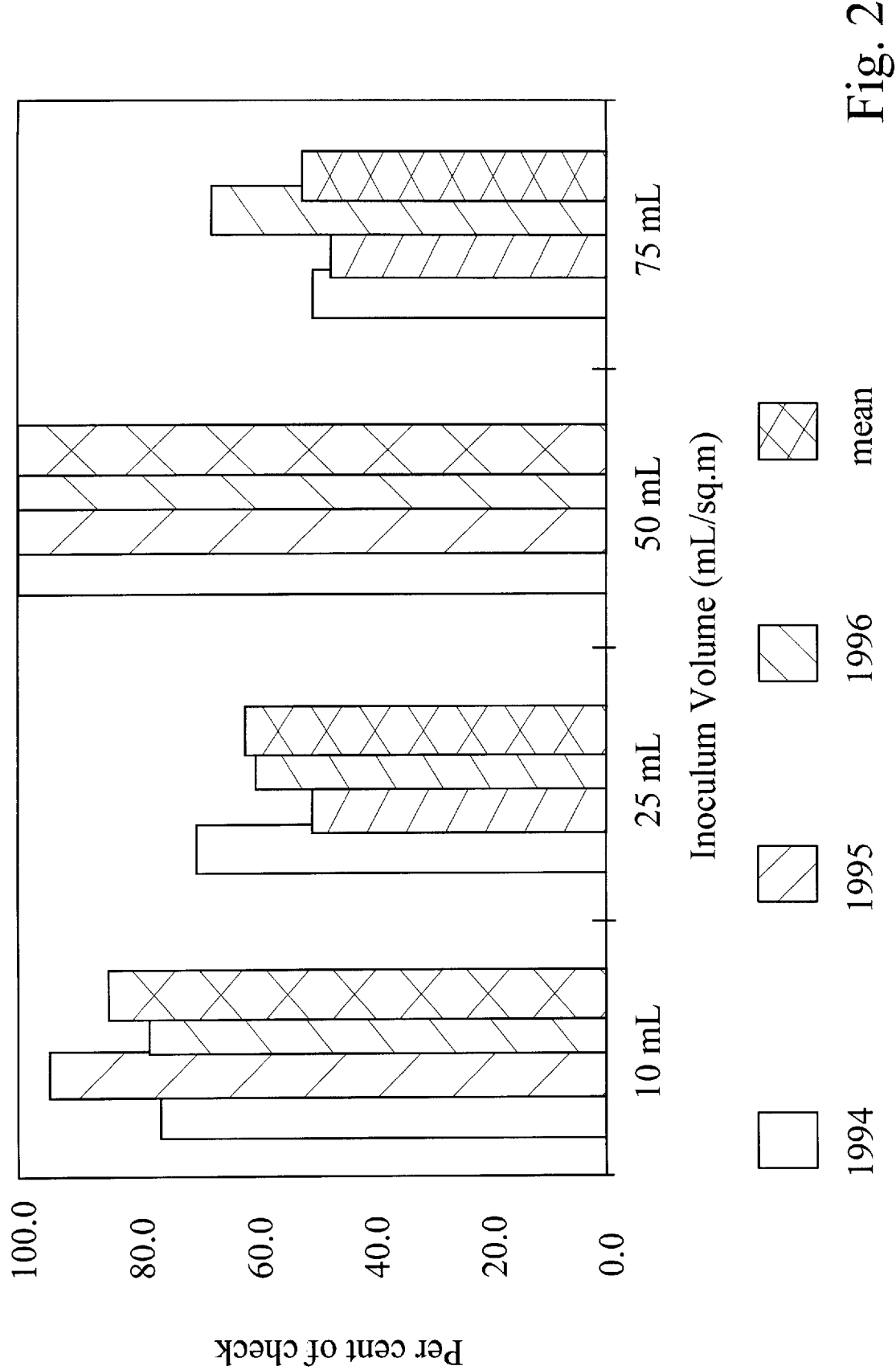
FIG. 2 is a graph which illustrates the effect of different volumes of LTB fungus infested grain on field grown *C. canadensis* foliar dry weight at 1, 2 and 3 years after application.

Field inoculations with the exception of one location were inconclusive. It is thought that this was likely due to rodents feeding on the inoculum as seed husks were found at some locations and/or poor inoculum. The treatments at site 63 near Whitecourt were found to provide some control. These plots have been monitored for three years and consistently show a reduction in foliar biomass compared to the check plots (FIG. 2.). It is our opinion that the 50 mL treatment most likely failed because of poor inoculum viability. The results indicate that the LTB fungus can reduce *C. canadensis* foliar biomass for up to three years after application. It appears that the 25 mL (15 g/L/m$^2$) and 75 mL (45 g/L/m$^2$) treatments give nearly the same level of control (40% versus 47% reduction in the biomass). This gives a measure of how much infested grain needs to be applied. Percent cover by *C. canadensis* was not measured in 1996 as this does not seem to give a consistent measure of the effect of the fungus on the grass, FIG. 1. This is most likely due to observer error in cover estimation.

Observations on non-target plants indicated that the LTB at very least did not reduce the density or species richness. In several of the locations the non-target plant species increased in species richness as well as in cover. This is an indication of species selectivity.

Because infested oat and rye grains appear to be attractive to rodents an alternative inoculum was sought. Results from the growth chamber study showed that both flour or flour coated wood is effective as inoculum. However, results from the second field trial indicate that inoculum applied as a flour may be just as effective as oat/rye grain inoculum in controlling the grass. Flour-coated wood was not as effective. The LTB infested flour is more attractive from an operational point of view than the oat/rye grain inoculum. In the study the flour was applied dry, however, it is expected that the flour could be suspended in water and applied as a spray.

The second growth chamber experiment showed that LTB isolates were more pathogenic to *C. canadensis* than the unidentified snow mould from Whitecourt. In the limited number of *C. canadensis* tested there were no apparent differences in susceptibility to either LTB isolates.

Conclusion

These results show that a selected strain of LTB snow mould, (≡*Coprinus psychromorbidus*) (ATCC Deposit no 74407) is an effective bio-control agent for *C. canadensis*.

The fungus can reduce grass foliar biomass for up to three years after a single application. LTB infested flour is just as an effective inoculum source as oat/rye grains. The LTB isolates of (≡*C. psychromorbidus*) tested appear to be equally as pathogenic to *C. canadensis*.

I claim:

1. A method for suppressing the growth of *C. canadensis*, comprising applying thereto or to a locus thereof, in the autumn, an effective amount of a composition comprising the low temperature basidiomycete fungus having all of the identifying characteristics of *Coprinus psychromorbidus* ATCC Deposit 74407, and a cereal grain carrier which is an agriculturally acceptable carrier and is capable of supporting the growth of the fungus, wherein prior to application to the plant or locus thereof the fungus is grown on the carrier which has been sterilized in the dark at about 15° C. until the carrier is substantially thoroughly colonized by the fungus.

2. A method according to claim 1, wherein the composition the carrier is a sterilized mixture of rye and oat grains comprising 50–100%/w of rye and 50–0%/w of oat.

3. A method according to claim 2, wherein the carrier comprises 50%/w of rye and 50%/w of oat grains.

4. A method according to claim 3, wherein the grains are ground to a flour after colonization by the fungus.

5. A method according to claim 4, wherein the flour is of a particle size that will pass through a 0.25 mm sieve.

6. A method according to claim 2, wherein the composition is applied in the form of the grain, or as a flour.

7. A method according to claim 6, wherein the grain or flour is suspended in water and applied as a spray.

8. A method according to claim 2, wherein the rate of application of the composition is 6–50 $g/L/m^2$.

9. A method according to claim 8, wherein the rate of application is about 30 $g/L/m^2$.

* * * * *